United States Patent
Saito et al.

(10) Patent No.: US 12,171,573 B2
(45) Date of Patent: Dec. 24, 2024

(54) BLOOD VESSEL POSITION DISPLAY DEVICE AND BLOOD VESSEL POSITION DISPLAY METHOD

(71) Applicants: Kabushiki Kaisha Nihon Micronics, Tokyo (JP); Hirosaki University, Aomori (JP)

(72) Inventors: Yuki Saito, Saitama (JP); Yoshiyuki Fukami, Ibaraki (JP); Hiroshi Kamiya, Kanagawa (JP); Osamu Arai, Tochigi (JP); Kazuhiko Sasagawa, Aomori (JP); Koichi Sagawa, Aomori (JP); Yasutaka Hanada, Aomori (JP); Toshiro Ono, Kanagawa (JP)

(73) Assignee: Kabushiki Kaisha Nihon Micronics, Musashino (JP)

(*) Notice: Subject to any disclaimer, the term of this patent is extended or adjusted under 35 U.S.C. 154(b) by 284 days.

(21) Appl. No.: 17/611,075

(22) PCT Filed: Feb. 28, 2020

(86) PCT No.: PCT/JP2020/008317
§ 371 (c)(1),
(2) Date: Nov. 12, 2021

(87) PCT Pub. No.: WO2020/230407
PCT Pub. Date: Nov. 19, 2020

(65) Prior Publication Data
US 2022/0249016 A1    Aug. 11, 2022

(30) Foreign Application Priority Data
May 15, 2019    (JP) .................. 2019-091841

(51) Int. Cl.
*A61B 5/00*    (2006.01)
*A61M 5/42*    (2006.01)

(52) U.S. Cl.
CPC ............ *A61B 5/489* (2013.01); *A61B 5/0071* (2013.01); *A61B 5/0077* (2013.01); *A61M 5/427* (2013.01)

(58) Field of Classification Search
CPC ...... A61B 5/489; A61B 5/0059; A61B 5/0062; A61B 5/0064; A61B 5/0077; A61B 5/0082
See application file for complete search history.

(56) References Cited

U.S. PATENT DOCUMENTS

| | | |
|---|---|---|
| 6,556,858 B1 | 4/2003 | Zeman |
| 11,200,977 B2 | 12/2021 | Sakamoto et al. |

(Continued)

FOREIGN PATENT DOCUMENTS

| | | |
|---|---|---|
| JP | 2006102360 A | 4/2006 |
| JP | 2008253494 A | 10/2008 |

(Continued)

*Primary Examiner* — Carolyn A Pehlke
(74) *Attorney, Agent, or Firm* — Lorenz & Kopf, LLP

(57) ABSTRACT

A blood vessel position display device (1) includes an image processing device (31) configured to subject an image for analysis of a target part (2) to image processing to acquire blood vessel information including positions and shapes of blood vessels included in the target part (2), a selection device (32) configured to choose blood vessels as conforming blood vessels in which a parameter obtained from the blood vessel information satisfies specific conditions, an image generation device (33) configured to generate a projection image including display lines at least set to have lengths corresponding to the conforming blood vessels, and a projection device (40) configured to cause the positions of the display lines to correspond to the positions of the conforming blood vessels so as to project the projection image on the target part (2).

20 Claims, 7 Drawing Sheets

(56) References Cited

U.S. PATENT DOCUMENTS

| | | | |
|---|---|---|---|
| 2007/0038118 A1* | 2/2007 | DePue | A61B 5/0059 600/476 |
| 2012/0148135 A1 | 6/2012 | Van Rens et al. | |
| 2012/0190981 A1* | 7/2012 | Harris | A61B 5/150946 604/95.01 |
| 2015/0051460 A1* | 2/2015 | Saxena | A61B 5/0059 600/407 |
| 2015/0209113 A1* | 7/2015 | Burkholz | A61B 5/743 600/417 |
| 2016/0354030 A1 | 12/2016 | Tang et al. | |
| 2019/0038111 A1 | 2/2019 | Endo | |
| 2021/0228151 A1* | 7/2021 | Wang | A61B 5/489 |

FOREIGN PATENT DOCUMENTS

| | | |
|---|---|---|
| JP | 4555534 B2 | 10/2010 |
| JP | 2013501567 A | 1/2013 |
| JP | 2014233521 A | 12/2014 |
| JP | 6127207 B2 | 5/2017 |
| JP | 2017080398 A | 5/2017 |
| TW | 201813589 A | 4/2018 |
| WO | WO2017183307 A1 | 10/2017 |

\* cited by examiner

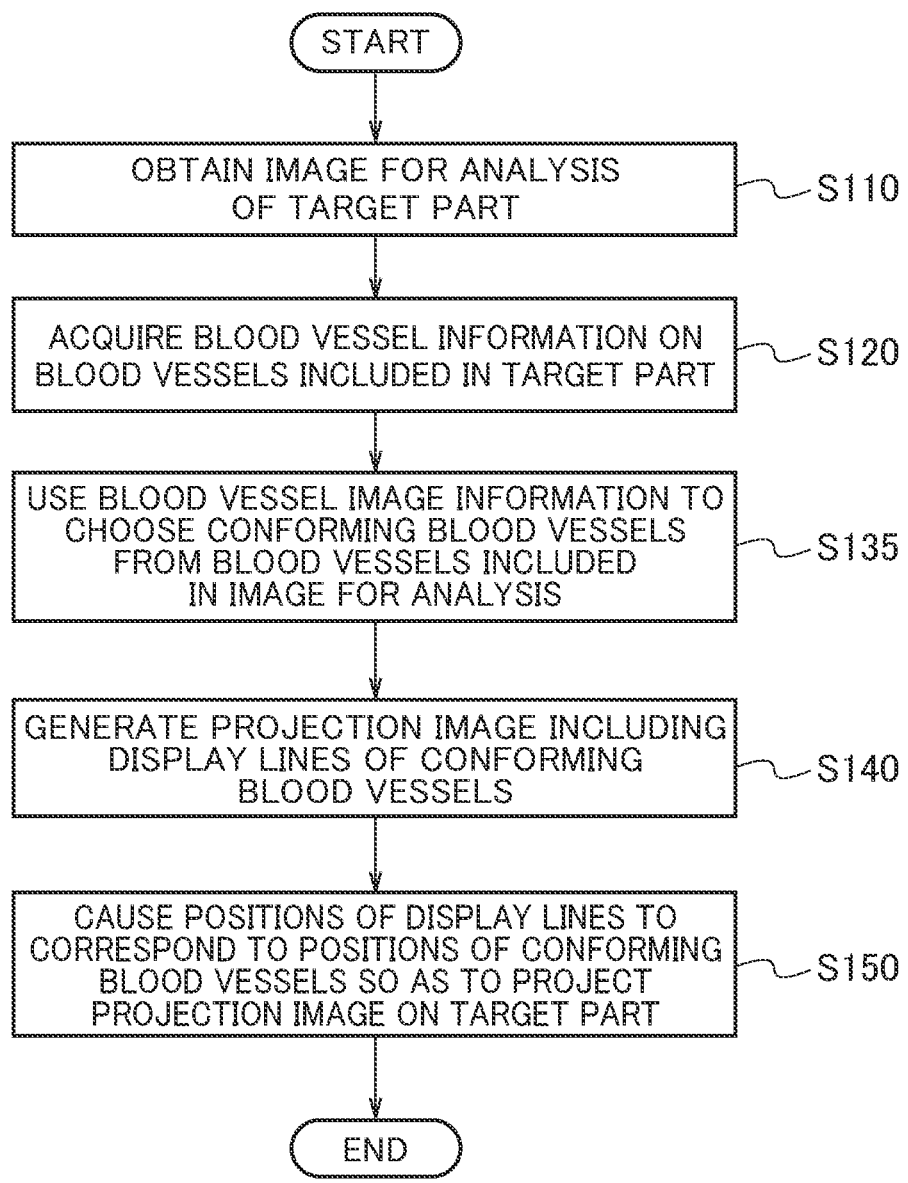

BLOOD VESSEL POSITION DISPLAY DEVICE AND BLOOD VESSEL POSITION DISPLAY METHOD

TECHNICAL FIELD

The present invention relates to a blood vessel position display device and a blood vessel position display method for displaying positions of blood vessels.

BACKGROUND ART

A system is disclosed that displays positions of blood vessels obtained from an image indicating a part of a human body (refer to Patent Literature 1 and Patent Literature 2). A method is known, for example, that captures a part irradiated with a near infrared light by an infrared camera so as to visualize the blood vessels while taking advantage of the properties of hemoglobin that absorbs the near infrared light.

CITATION LIST

Patent Literature

Patent Literature 1: Japanese Patent No. 4555534
Patent Literature 2: Japanese Patent No. 6127207

SUMMARY OF THE INVENTION

Technical Problem

No conventional systems disclose a method that not only visualizes blood vessels but also displays positions of blood vessels conforming to a particular purpose. A method of displaying the positions of the blood vessels suitable for needle puncture for collecting blood, for example, still needs to be developed.

In response to this issue, the present invention provides a blood vessel position display device and a blood vessel position display method capable of displaying positions of blood vessels conforming to a particular purpose.

Solution to Problem

An aspect of the present invention provides a blood vessel position display device including an image processing device configured to subject an image for analysis of a target part to image processing to acquire blood vessel information including positions and shapes of blood vessels included in the target part, a selection device configured to choose a blood vessel as a conforming blood vessel in which a parameter obtained from the blood vessel information satisfies a specific condition, an image generation device configured to generate a projection image including a display line at least set to have a length corresponding to the conforming blood vessel, and a projection device configured to cause a position of the display line to correspond to a position of the conforming blood vessel so as to project the projection image on the target part.

Another aspect of the present invention provides a blood vessel position display method including subjecting an image for analysis of a target part to image processing to acquire blood vessel information including positions and shapes of blood vessels included in the target part, choosing a blood vessel as a conforming blood vessel in which a parameter obtained from the blood vessel information satisfies a specific condition, generating a projection image including a display line at least set to have a length corresponding to the conforming blood vessel, and causing a position of the display line to correspond to a position of the conforming blood vessel so as to project the projection image on the target part.

Advantageous Effects of the Invention

The present invention can provide the blood vessel position display device and the blood vessel position display method capable of displaying the positions of the blood vessels conforming to a particular purpose.

BRIEF DESCRIPTION OF DRAWINGS

FIG. 11 is a flowchart for explaining a blood vessel position display method according to the second embodiment of the present invention.

DESCRIPTION OF EMBODIMENTS

Figure 1:
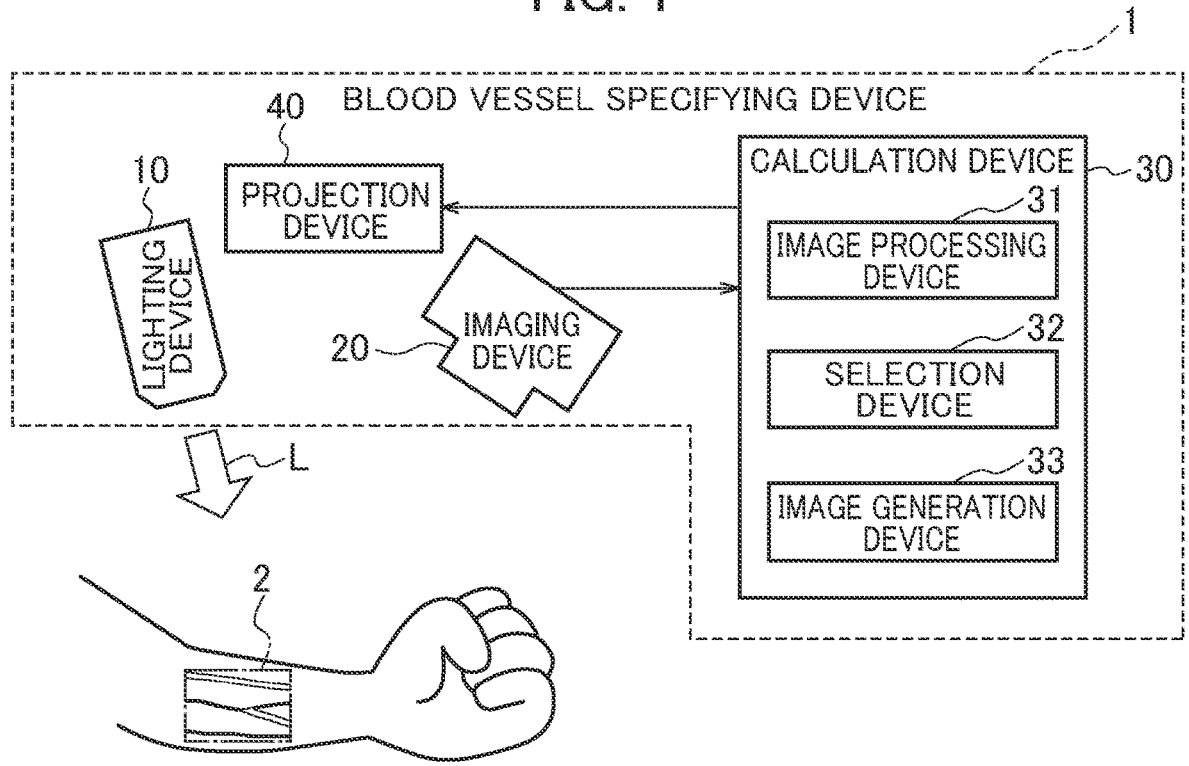
FIG. 1 is a schematic view illustrating a configuration of a blood vessel position display device according to a first embodiment of the present invention.

Some embodiments of the present invention are described below with reference to the drawings. The same or similar elements illustrated in the drawings are denoted below by the same or similar reference numerals. It should be understood that the drawings are shown as schematic illustrations. It should also be understood that the embodiments described below illustrate devices and methods for embodying the technical idea of the present invention, but are not intended to be limited to the structures or arrangements of the constituent elements as described herein. Various modifications can be made to the respective embodiments according to the present invention in terms of the appended claims.

First Embodiment

A blood vessel position display device according to a first embodiment of the present invention displays positions of blood vessels conforming to a particular purpose chosen from blood vessels included in a target part to be sampled. The following explanations are made with regard to a case in which a part of a forearm of a human body is a target part 2, as illustrated in FIG. 1. The blood vessel position display device 1 illustrated in FIG. 1 includes a lighting device 10, an imaging device 20, a calculation device 30, and a projection device 40. The calculation device 30 includes an image processing device 31, a selection device 32, and an image generation device 33.

The lighting device 10 irradiates the target part 2 with an irradiation light L having a specific wavelength. The imaging device 20 captures the target part 2 including a region around blood vessels to obtain an image for analysis of the target part 2. The calculation device 30 chooses blood vessels, as "conforming blood vessels", that satisfy specific conditions from blood vessels included in the target part 2 based on the image for analysis. The calculation unit 30 also generates a projection image including display lines of the conforming blood vessels. The projection image generated by the calculation device 30 is projected on the target part 2 by the projection device 40. The blood vessel position display device 1 is described in more detail below.

The wavelength of the irradiation light L emitted from the lighting device 10 is determined such that the imaging device 20 can capture the image for analysis in which boundaries between the blood vessels and the other regions are more distinct in the target part 2 irradiated with the irradiation light L than in the other part not irradiated with the irradiation light L. For example, a near infrared light having a wavelength in a range of about 800 nm to 900 nm may be used as the irradiation light L so as to take advantage of the properties of hemoglobin that absorbs the near infrared light. In the case of the near infrared light used as the irradiation light L, an infrared camera is preferably used as the imaging device 20. The use of the infrared camera can capture the image for analysis in which the blood vessels are imaged in black, and the other regions such as skin are imaged in white.

The target part 2 is not necessarily irradiated with the irradiation light L when the image for analysis can be captured in which the boundaries between the blood vessels and the other regions are distinct without the irradiation with the irradiation light L.

The image for analysis in the target part 2 captured by the imaging device 20 is sent to the image processing device 31. The image processing device 31 subjects the image for analysis to image processing so as to acquire blood vessel information including the positions and the shapes of the blood vessels included in the target part 2.

Figure 2:
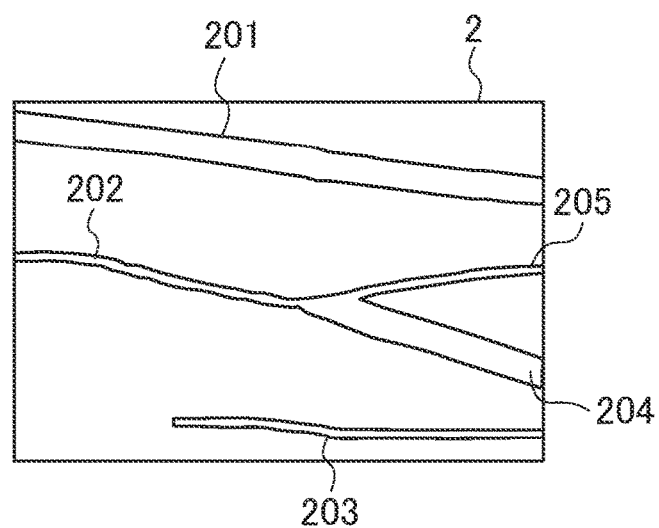
FIG. 2 is a schematic view showing an example of blood vessels included in a target part.

FIG. 2 illustrates blood vessel images of the blood vessels included in the target part 2 obtained through the image processing. FIG. 2 shows an example in which the blood vessel information on the blood vessels 201 to 205 is acquired. The blood vessel information could include a region in which the blood vessel images cannot be obtained regardless of the presence of the blood vessels under the skin in the target part 2. Such a region is presumed to be a region in which the irradiation light L is weak, a region in which sensitivity of a light detection unit of the imaging device is low, or a region in which absorption of light by blood is not exerted strongly for a reason that the blood vessels are located at deep parts, for example. When a blood vessel is branched, the image processing device 31 acquires the blood vessel information such that a region from the branched part to an edge confirmable from the image for analysis is defined as one blood vessel. Namely, the blood vessel information is acquired for each blood vessel in which the region from the branched part to each edge is defined as the corresponding single blood vessel.

The image processing device 31 binarizes the image for analysis in accordance with a difference in luminance between a region under which blood vessels are present (referred to below as a "blood vessel region") and any other region under which blood vessels are not present (referred to below as "other region"), and distinguishes the blood vessel region from the other region so as to acquire the blood vessel information. The blood vessel images are shown darkly in the blood vessel region because of the absorption of light by the blood vessels. The image processing device 31 may binarize the image for analysis after executing image processing of emphasizing the contrast between the blood vessel region and the other region.

The selection device 32 chooses blood vessel images that satisfy specific conditions from the blood vessel images included in the image for analysis in accordance with a selection standard that is a parameter falling within a specific range effective for a particular purpose (referred to below as a "selection parameter"). In particular, the selection device 32 compares the selection parameter acquired from the blood vessel information with a decision value, and chooses the blood vessel images in which the selection parameter satisfies the decision value.

The selection parameter compared with the decision value is determined depending on the intention of choosing the blood vessels. For example, when the intention is to choose the blood vessels easy to puncture by a needle, a parameter indicating the easiness of the needle puncture is used as the selection parameter. Examples of parameters compared with the decision value include straightness of the blood vessels, an extending direction of the blood vessels, a length of the blood vessels, and a thickness of the blood vessels. The reason for using these parameters is as follows.

The needle puncture to a blood vessel is more difficult as the straightness of the blood vessel is lower. The blood vessel having higher straightness is thus preferably chosen for the needle puncture. The needle puncture is sometimes easier in a specific direction than in any other direction depending on the site of the blood vessel. For example, the needle puncture is easily performed on a forearm typically in the direction from the wrist to the elbow. The blood vessel is thus often easier to puncture by a needle in a particular direction that is the extending direction of the blood vessel. In addition, the blood vessel preferably has a predetermined length or longer, since the needle puncture is difficult when the blood vessel is too short. The blood vessel also preferably has a predetermined thickness or greater, since the needle puncture is easier as the blood vessel is thicker.

As described above, the selection device 32 compares the selection parameter suitable for the intention of choosing the blood vessels with the decision value set to conform to the intention. The selection device 32 chooses the blood vessels as the conforming blood vessels in which the selection parameter satisfies the decision value.

An example is described below in which the selection device 32 chooses the parameter indicating the easiness of the needle puncture as the selection parameter so as to specify the blood vessels easy to puncture by a needle among the blood vessels 201 to 205 illustrated in FIG. 2. The selection parameter to be used below is the straightness of the blood vessels, the extending direction of the blood vessels, the length of the blood vessels, or the thickness of the blood vessels.

Figure 3:
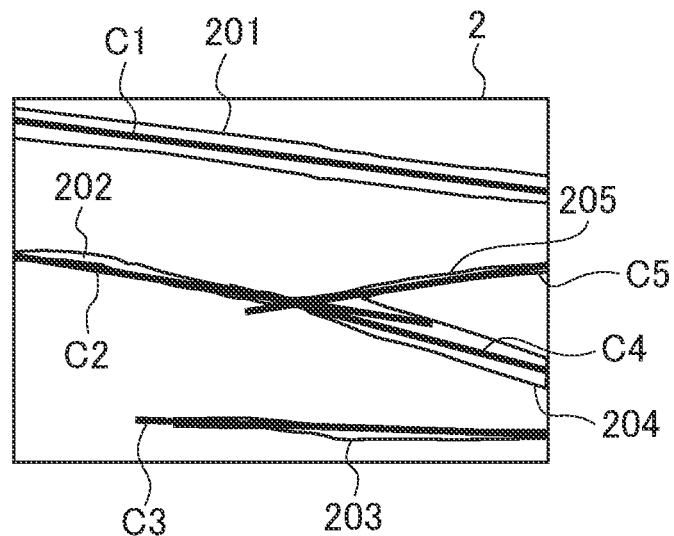
FIG. 3 is a schematic view showing an example of approximate lines of blood vessels created by the blood vessel position display device according to the first embodiment of the present invention.

In the case of using the straightness of the blood vessels as the selection parameter, the selection device 32 creates approximate lines C1 to C5 corresponding to the blood vessel images 201 to 205, as illustrated in FIG. 3. For example, the selection device 32 reduces the width of the blood vessel images 201 to 205 in the binary image for analysis to 1 pixel by thinning the lines and creates the approximate lines C1 to C5 by use of the method of least squares and the like. The selection device 32 then compares a coefficient of determination (R2) obtained for the respective approximate lines C1 to C5 with the decision value. The blood vessels with the coefficient of determination closer to one have the higher straightness and is easier to puncture by a needle. The decision value of the coefficient of determination is herein set to 0.7 or greater (decision condition 1), for example.

In the case of using the extending direction of the blood vessels as the selection parameter, the selection device 32 uses the approximate lines described above to specify the extending direction of the respective blood vessel images. The blood vessels are preferably chosen that each have a smaller angle between the extending direction of the approximate line and the direction suitable for a particular purpose (referred to below as a "decision angle"). The decision value of the decision angle is herein set to −20 degrees as the minimum value and set to 20 degrees as the maximum value (decision condition 2), for example. The image for analysis may be obtained such that the direction suitable for a particular purpose and the horizontal direction of the image for analysis are parallel to each other so as to specify the extending direction of the respective blood vessel images.

In the case of using the length of the blood vessels as the selection parameter, a distance between one end to the other end of each blood vessel image displayed in the image for analysis is defined as the length of the respective blood vessels. For example, the number of pixels of the approximate line of one pixel width obtained through the thinning processing performed on each blood vessel image may be used as the length of the blood vessel. The longer blood vessel is easier to puncture by a needle. The minimum value of the decision value for the length of each blood vessel is set to 10 mm (decision condition 3), for example. The maximum value of the decision value may also be set for the length of the blood vessel if any problem arises because the blood vessel is too long.

In the case of using the thickness of the blood vessels as the selection parameter, the selection device 32 compares the width of the respective blood vessel images displayed in the image for analysis with the decision value. Alternatively, the selection device 32 may use the approximate lines created as described above to calculate the width of the respective blood vessel images. In particular, a perpendicular is drawn to the circumference from the approximate line, and the length of the part in which the perpendicular and the blood vessel image overlap with each other is defined as the thickness of the blood vessel. The thicker blood vessel is easier to puncture by a needle. The minimum value of the decision value for the thickness of each blood vessel is set to 2 mm (decision condition 4), for example. The maximum value of the decision value may also be set for the thickness of the blood vessel if any problem arises because the blood vessel is too thick. When the thickness of the respective blood vessels varies, the thickest part or the thinnest part may be defined as the thickness of each blood vessel, or the average may be defined as the thickness of the respective blood vessels.

The selection device 32 compares the selection parameter with the decision value with respect to all of the blood vessel images included in the image for analysis. The selection device 32 chooses, as the conforming blood vessels, the blood vessels in which the selection parameter satisfies the decision value. For example, the selection device 32 determines whether all of the decision conditions 1 to 4 are satisfied in the respective blood vessel images 201 to 205 included in the target part 2. The conforming blood vessels may be chosen only in accordance with the particularly important selection parameter, instead of the use of all of the decision conditions 1 to 4. For example, at least one of the straightness of the blood vessels, the extending direction of the blood vessels, the length of the blood vessels, and the thickness of the blood vessels may be used as the selection parameter so as to choose the conforming blood vessels.

Figure 4:
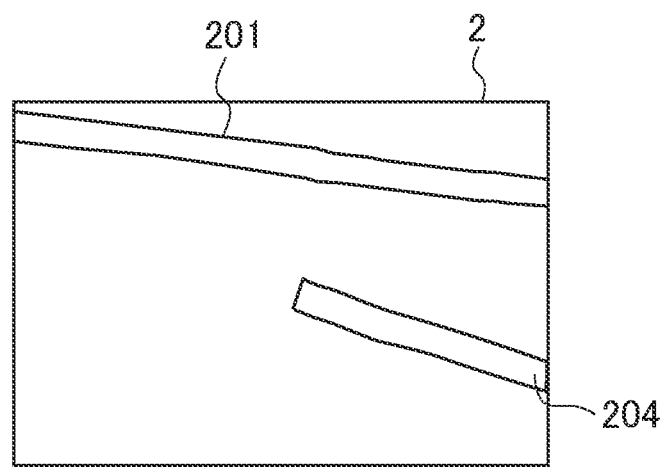
FIG. 4 is a schematic view illustrating blood vessels chosen by the blood vessel position display device according to the first embodiment of the present invention.

As described above, the selection device 32 chooses the blood vessels in which the selection parameter satisfies the specific conditions as the conforming blood vessels. FIG. 4 illustrates a case in which the blood vessel image 201 and the blood vessel image 204 are chosen as the conforming blood vessels from the blood vessel images illustrated in FIG. 2.

The image generation device 33 generates a projection image including display lines at least set to have the lengths corresponding to the conforming blood vessels chosen by the selection device 32. An example of generating the projection image including the display lines of the conforming blood vessels illustrated in FIG. 4 is described below.

Figure 5:
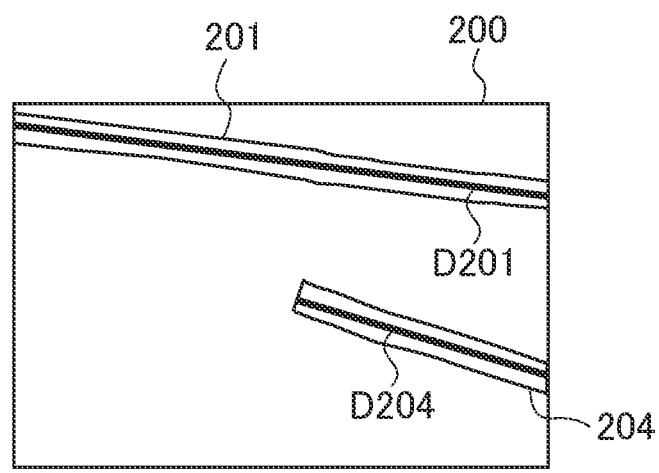
FIG. 5 is a schematic view showing an example of display lines of blood vessels created by the blood vessel position display device according to the first embodiment of the present invention.
Figure 6:
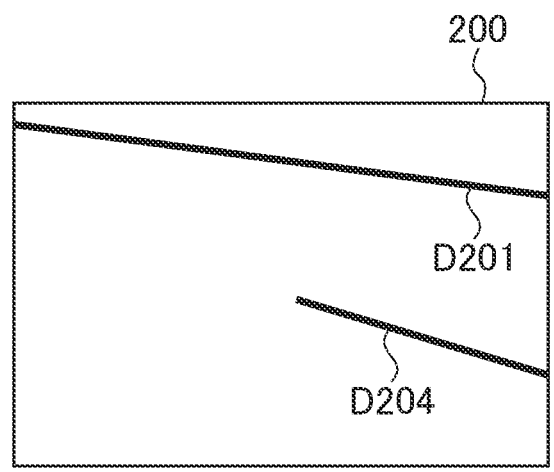
FIG. 6 is a schematic view showing an example of a projection image generated by the blood vessel position display device according to the first embodiment of the present invention.

First, the image generation device 33 creates a display line D201 and a display line D204 having the lengths equal to those of the blood vessel image 201 and the blood vessel image 204 in the image for analysis. The actual shape of each blood vessel is simplified to create a display line such that, for example, a straight display line is created for the blood vessel when having the high straightness. When the blood vessel image has curved parts, for example, the shape may be simplified to create a display line including curved lines or plural straight lines connected and combined with each other. The image generation device 33 generates the projection image 200 in which the display line D201 and the display line D204 respectively overlap with the blood vessel image 201 and the blood vessel image 204, as illustrated in FIG. 5. The image generation device 33 then deletes the blood vessel image 201 and the blood vessel image 204 from the projection image 200 while leaving the display line D201 and the display line D204, as illustrated in FIG. 6.

Figure 7:
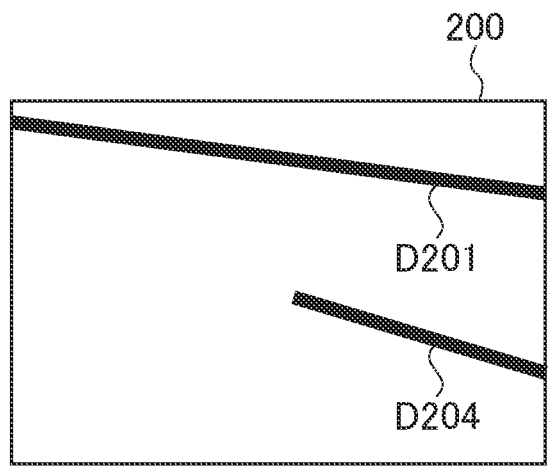
FIG. 7 is a schematic view showing an example of the thickened display lines in the projection image.

The image generation device 33 then thickens the display line D201 and the display line D204 so as to have predetermined widths in the projection image 200, as illustrated in FIG. 7. Thickening the widths facilitates the visual recognition of the display line D201 and the display line D204. The thickening increases the width of the respective display lines to a level easy to visually recognize, for example. The display lines are not necessarily thickened when easily visually recognized without subjected to the thickening.

The generation of the projection image by the image generation device 33 is thus completed. The image generation device 33 sends the projection image to the projection device 40.

Figure 8:
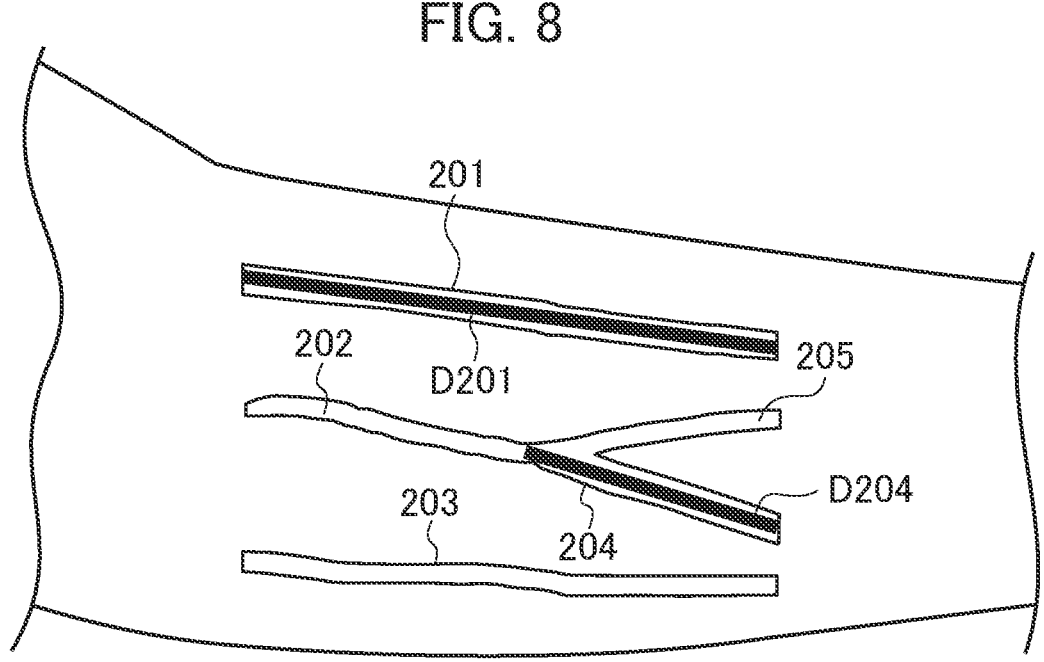
FIG. 8 is a schematic view showing an example of the projection image generated and projected on the target part by the blood vessel position display device according to the first embodiment of the present invention.

The projection device 40 projects the projection image sent from the image generation device 33 on the target part 2 while causing the positions of the display lines to correspond to the positions of the conforming blood vessels, as illustrated in FIG. 8. FIG. 8 illustrates a case in which the projection image including the display line D201 and the display line D204 is projected on the target part 2 in which the display line D201 overlaps with the blood vessel image 201 and the display line D204 overlaps with the blood vessel image 204. The blood vessel position display device 1 as described above thus can display, on the target part 2, the display lines of the blood vessels having the simplified shapes and overlapping with the positions of the corresponding blood vessels.

Figure 9:
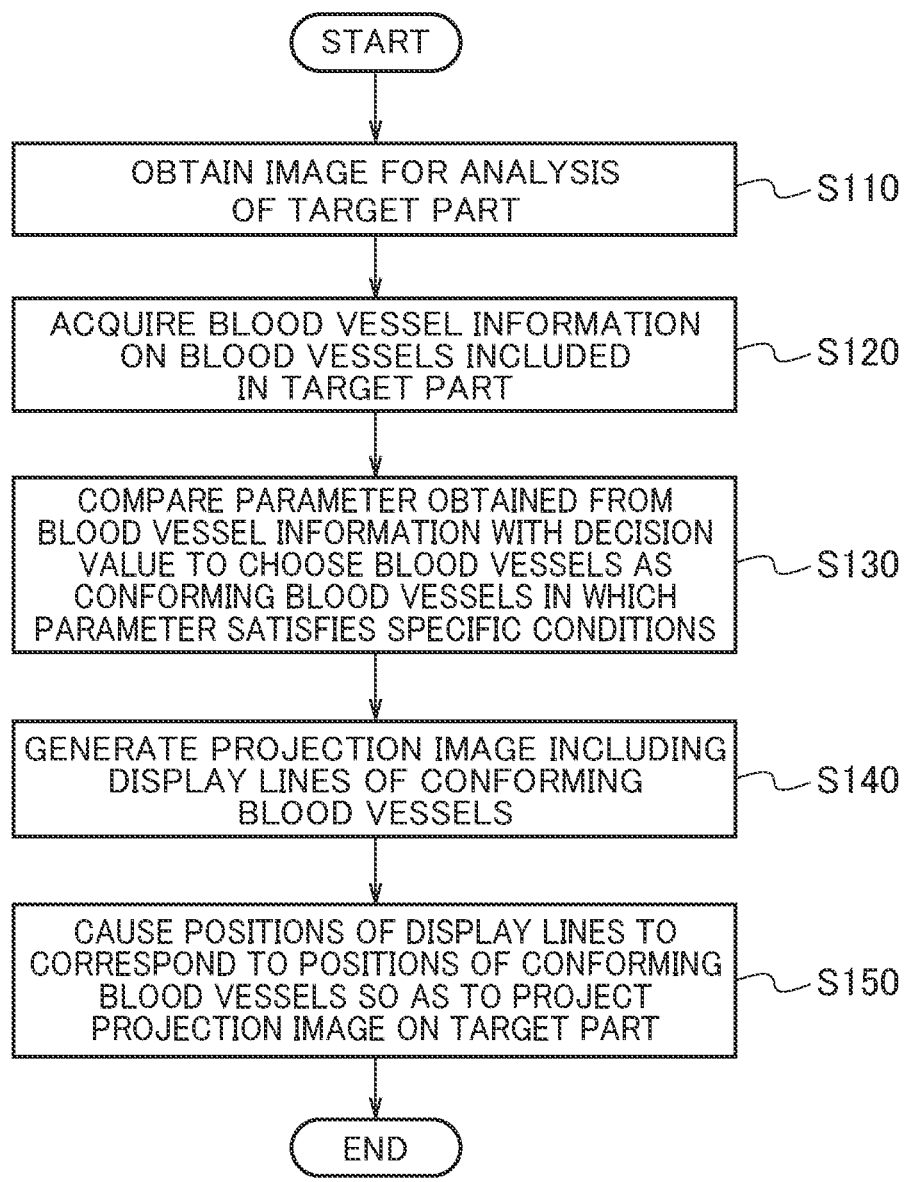
FIG. 9 is a flowchart for explaining a blood vessel position display method according to the first embodiment of the present invention.

FIG. 9 is a flowchart for explaining a series of processing by a blood vessel position display method by use of the blood vessel position display device 1.

In step S110 in the flowchart shown in FIG. 9, the imaging device 20 obtains the image for analysis of the target part 2. The lighting device 10 at this point may irradiate the target part 2 with the irradiation light L having a specific wavelength.

In step S120, the image processing device 31 subjects the image for analysis to the image processing so as to acquire the blood vessel information including the positions and the shapes of the blood vessels included in the target part 2. In step S130, the selection device 32 compares the selection parameter obtained from the blood vessel information with the decision value, and chooses the blood vessels in which the selection parameter satisfies the specific conditions as the conforming blood vessels. In step S140, the image generation device 33 generates the projection image including the display lines of the conforming blood vessels in which the display lines are at least set to have the lengths corresponding to the conforming blood vessels.

In step S150, the projection device 40 causes the positions of the display lines to correspond to the positions of the conforming blood vessels so as to project the projection image on the target part 2.

As described above, the blood vessel position display device 1 according to the first embodiment projects the display lines having the simplified shapes of the conforming blood vessels on the target part 2 in which the display lines and the conforming blood vessels are caused to overlap with each other. The blood vessel position display device 1 displays, on the target part 2, the clarified and simplified positions of the blood vessels in which the selection parameter satisfies the particular conditions, so as to easily specify the blood vessels conforming to a particular purpose.

Second Embodiment

Figure 10:
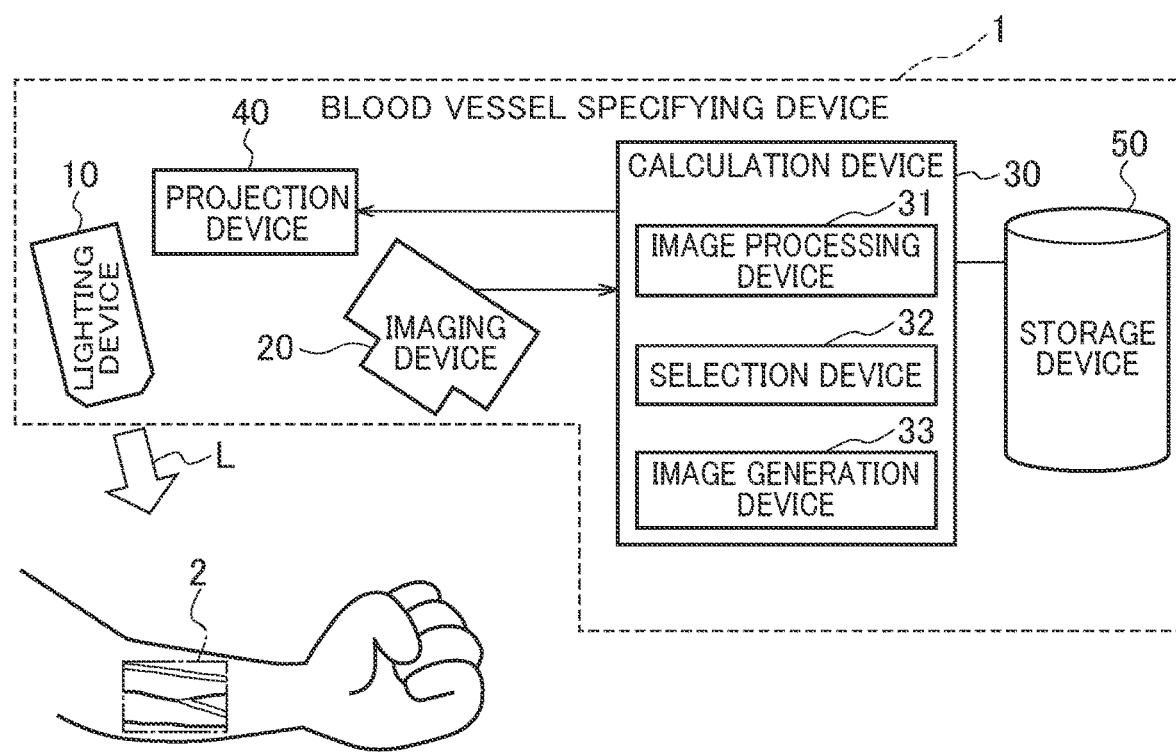
FIG. 10 is a schematic view illustrating a configuration of a blood vessel position display device according to a second embodiment of the present invention.

FIG. 10 illustrates a configuration of the blood vessel position display device 1 according to a second embodiment. The blood vessel position display device 1 illustrated in FIG. 10 further includes a storage device 50 that stores blood vessel image information on images of blood vessels that are made into a database in which the selection parameter satisfies the specific conditions. The other elements of the blood vessel position display device 1 illustrated in FIG. 10 are the same as those in the first embodiment illustrated in FIG. 1.

The blood vessel image information is stored such that image information on blood vessels having various shapes is made into a database for each purpose in which the selection parameter is determined to fall within a specific range effective for a particular purpose. The selection device 32 refers to the blood vessel image information made into the database, and compares the blood vessel images included in the image for analysis of the target part 2 with the images of the blood vessels in which the selection parameter is determined to fall within the specific range effective for a particular purpose (referred to as "appropriate blood vessels"). The selection device 32 then chooses, from the blood vessel images included in the image for analysis, the blood vessels as the conforming blood vessels in which the blood vessel images conform to any of the images of the appropriate blood vessels.

The blood vessel position display device 1 according to the second embodiment differs in choosing the conforming blood vessels by use of the blood vessel image information including the appropriate blood vessels made into the database from the blood vessel position display device 1 according to the first embodiment that compares the selection parameter with the decision value to choose the conforming blood vessels. The other configurations are substantially the same as those in the first embodiment, and overlapping explanations are not repeated below.

FIG. 11 is a flowchart explaining a series of processing by a blood vessel position display method by use of the blood vessel position display device 1 according to the second embodiment.

The blood vessel information on the blood vessels included in the target part 2 is acquired in the processing in step S110 and step S120 in the flowchart shown in FIG. 11, in the same manner as the processing in step S110 and step S120 in the flowchart shown in FIG. 9. In step S135 in FIG. 11, the selection device 32 uses the blood vessel image information to choose the conforming blood vessels from the blood vessel images included in the image for analysis.

The projection image including the display lines of the conforming blood vessels is then generated so as to be projected on the target part 2 in the processing in step S140 and S150 in the flowchart shown in FIG. 11, in the same manner as the processing in step S140 and S150 in the flowchart shown in FIG. 9.

The blood vessel position display device 1 according to the second embodiment can make the image information on a large number of appropriate blood vessels into a database for each purpose, so as to choose the conforming blood vessels by use of artificial intelligence (AI), for example.

Other Embodiments

While the present invention has been described above with reference to the respective embodiments, it should be understood that the present invention is not intended to be limited to the descriptions and the drawings composing part of this disclosure. Various alternative embodiments, examples, and technical applications will be apparent to those skilled in the art according to this disclosure.

For example, the calculation device 30 of the blood vessel position display device 1 may be installed at a place distant from a location for capturing the target part 2.

It should be understood that the present invention includes various embodiments not disclosed herein.

What is claimed is:

1. A blood vessel position display device comprising:
   an image processing device configured to subject an image including blood vessel images for analysis of a target part to image processing to acquire blood vessel information including positions and shapes of blood vessels included in the target part by
   reducing the width of blood vessel images to generate thinned blood vessel images;
   creating approximate lines corresponding to the thinned blood vessel images;
   obtaining a coefficient of determination for each approximate line; and
   comparing the coefficient of determination for each approximate line with a decision value;

a selection device configured to choose a blood vessel as a conforming blood vessel in which a parameter obtained from the blood vessel information satisfies a specific condition based on the respective coefficient of determination;

an image generation device configured to generate a projection image including a chosen blood vessel image and a display line at least set to have a length corresponding to the conforming blood vessel; and a projection device configured to cause a position of the display line to correspond to a position of the conforming blood vessel so as to project the projection image directly on to the target part, wherein the image generation device is configured to delete the chosen blood vessel image from the projection image.

2. The blood vessel position display device according to claim 1, wherein the parameter indicates easiness of needle puncture to the blood vessels, and wherein the selection device uses the parameter that indicates easiness of needle puncture to the blood vessels so as to choose the conforming blood vessel.

3. The blood vessel position display device according to claim 2, wherein the selection device uses at least one of straightness of the blood vessels, an extending direction of the blood vessels, a length of the blood vessels, and a thickness of the blood vessels as the parameter so as to choose the conforming blood vessel.

4. The blood vessel position display device according to claim 1, wherein the image processing device performs binarization on the image for analysis to distinguish a region under which the blood vessels are present from another region so as to acquire the blood vessel information.

5. The blood vessel position display device according to claim 1, wherein the selection device compares the parameter obtained from the blood vessel information with a decision value so as to choose the conforming blood vessel.

6. The blood vessel position display device according to claim 1, wherein the selection device uses a database of stored blood vessel image information in which the parameter satisfies the specific condition so as to choose the conforming blood vessel.

7. The blood vessel position display device according to claim 1, further comprising:

a lighting device configured to irradiate the target part with an irradiation light having a specific wavelength; and an imaging device configured to capture the target part to obtain the image for analysis, wherein the specific wavelength is determined so that the imaging device obtains the image for analysis in which boundaries between the blood vessels and other regions are more distinct in the target part irradiated with the irradiation light than in another part not irradiated with the irradiation light.

8. The blood vessel position display device according to claim 7, wherein the irradiation light is a near infrared light.

9. A blood vessel position display method comprising:

subjecting an image including blood vessel images for analysis of a target part to image processing to acquire blood vessel information including positions and shapes of blood vessels included in the target part by reducing the width of blood vessel images to generate thinned blood vessel images;

creating approximate lines corresponding to the thinned blood vessel images;

obtaining a coefficient of determination for each approximate line; and comparing the coefficient of determination for each approximate line with a decision value;

choosing a blood vessel as a conforming blood vessel in which a parameter obtained from the blood vessel information satisfies a specific condition based on the respective coefficient of determination;

generating a projection image including a chosen blood vessel image and a display line at least set to have a length corresponding to the conforming blood vessel;

causing a position of the chosen blood vessel image the display line to correspond to a position of the conforming blood vessel;

projecting the projection image directly on the target part; and deleting the chosen blood vessel image from the projection image.

10. The blood vessel position display method according to claim 9, wherein the parameter indicates easiness of needle puncture to the blood vessels, and wherein the parameter that indicates easiness of needle puncture to the blood vessels is used so as to choose the conforming blood vessel.

11. The blood vessel position display method according to claim 10, wherein at least one of straightness of the blood vessels, an extending direction of the blood vessels, a length of the blood vessels, and a thickness of the blood vessels is used as the parameter so as to choose the conforming blood vessel.

12. The blood vessel position display method according to claim 9, wherein binarization is performed on the image for analysis to distinguish a region under which the blood vessels are present from another region so as to acquire the blood vessel information.

13. The blood vessel position display method according to claim 9, wherein the parameter obtained from the blood vessel information is compared with a decision value so as to choose the conforming blood vessel.

14. The blood vessel position display method according to claim 9, wherein choosing the blood vessel as the conforming blood vessel comprises comparing the blood vessel to blood vessel image information stored in a database of blood vessels in which the parameter satisfies the specific condition.

15. The blood vessel position display method according to claim 9, further comprising irradiating the target part with an irradiation light having a specific wavelength to capture the target part so as to obtain the image for analysis, wherein the specific wavelength is determined so that the image for analysis is obtained in which boundaries between the blood vessels and other regions are more distinct in the target part irradiated with the irradiation light than in another part not irradiated with the irradiation light.

16. The blood vessel position display method according to claim 15, wherein the irradiation light is a near infrared light.

17. The blood vessel position display method according to claim 9, wherein straightness of the blood vessels is used as the parameter so as to choose the conforming blood vessel.

18. The blood vessel position display method according to claim 9, wherein extending direction of the blood vessels is used as the parameter so as to choose the conforming blood vessel.

19. The blood vessel position display device according to claim 1, wherein the selection device uses straightness of the blood vessels as the parameter so as to choose the conforming blood vessel.

20. The blood vessel position display device according to claim 1, wherein the selection device uses extending direction of the blood vessels as the parameter so as to choose the conforming blood vessel.

* * * * *